United States Patent [19]

Scholz et al.

[11] 4,130,563
[45] Dec. 19, 1978

[54] Δ4-OXAZOLIN-2-ONES AND PROCESS THEREFOR

[75] Inventors: Karl-Heinz Scholz; Willy Hartmann; Hans-Georg Heine, all of Krefeld, Germany

[73] Assignee: Bayer Aktiengesellschaft, Leverkusen, Germany

[21] Appl. No.: 770,259

[22] Filed: Feb. 18, 1977

[30] Foreign Application Priority Data

Mar. 13, 1976 [DE] Fed. Rep. of Germany ....... 2610676

[51] Int. Cl.² ............................................. C07D 263/38
[52] U.S. Cl. ................................ 260/307 C; 526/260; 542/438
[58] Field of Search ...................... 260/307C; 542/438

[56] References Cited

U.S. PATENT DOCUMENTS 3,879,410  4/1975  Bottari et al. .................... 260/307 C

FOREIGN PATENT DOCUMENTS 1001989  2/1957  Fed. Rep. of Germany.

OTHER PUBLICATIONS

Goeth et al.–C.A. 66, 94935w (1967).

*Primary Examiner*—Raymond V. Rush
*Attorney, Agent, or Firm*—Sprung, Felfe, Horn, Lynch & Kramer

[57] ABSTRACT

Compounds having the formula

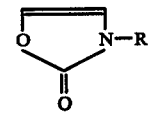

wherein R is hydrogen or an acyl radical are prepared by chlorinating 3-acyl-oxazolidin-2-ones, followed by dehydrochlorination and optionally by saponification and reacylation. The compounds are useful as starting material for substitution and addition reactions and as vinyl monomers in homo- and copolymerizations, whereby oxazolidin-2-one rings containing polymers are formed. These polymers can be used as antistatic agents, dyeing auxiliaries and ion exchangers.

2 Claims, No Drawings

Δ4-OXAZOLIN-2-ONES AND PROCESS THEREFOR

BACKGROUND

The invention relates to a new Δ⁴-oxazolin-2-ones and a process for their preparation.

As is known, the reaction of acyloines with carbamic acid derivatives or isocyanates leads to Δ⁴-oxazolin-2-ones which are substituted in the 4,5-position. For example, 4,5-dialkyl- and 4,5-diaryl-Δ⁴-oxazolin-2-ones have been obtained in this way (see Chem. Ber. 89, 1,748 (1956)). It is also known to prepare Δ⁴-oxazolin-2-ones which are alkylated in the 3-position from 4-halogeno-dioxol-2-ones and primary amines (see German Offenlegungsschrift 2,304,589). A further process which is known for the preparation of Δ⁴-oxazolin-2-ones is the photoisomerisation of 3-hydroxyisoxazoles: in connection with the isolation of active compounds of fly agaric which act on the central nervous system, muscazone, that is to say (Δ⁴-oxazolin-2-on-5-yl)-glycine, has been obtained by exposing ibotenic acid to light (Helv. Chim. Acta 50, 137 (1967)). However, the processes described for the preparation of the substituted Δ⁴-oxazolin-2-ones known hitherto cannot be used for synthesis of the parent compound, that is to say Δ⁴-oxazolin-2-one, and its N-acyl compounds, which have not been known hitherto.

SUMMARY

According to the present invention there is provided a Δ⁴-oxazolin-2-one of the formula

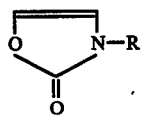

I in which
R represents hydrogen or an acyl radical of the formula R₁—CO—,
in which
R₁ denotes optionally substituted alkyl, alkenyl, cycloalkyl, aralkyl, aryl, alkoxy, aryloxy, alkylamino, dialkylamino or arylamino. Preferably, R₁ is methyl.

According to a further aspect of the invention there is provided a process for the preparation of a Δ⁴-oxazolin-2-one of the formula I wherein a

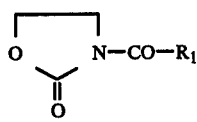

II in which
R₁ has the abovementioned meaning,
is chlorinated at a temperature from about 20° to about 150° C. in the presence of an agent which forms free radicals or in the presence of UV light, the chlorination product then being subjected to dehydrochlorination and the resulting 3-acyl-Δ⁴-oxazolin-2-one being optionally saponified in a known manner to give a Δ⁴-oxazolin-2-one and the latter being optionally reacylated in a known manner.

DESCRIPTION

The process according to the invention can be illustrated by the equation which follows:

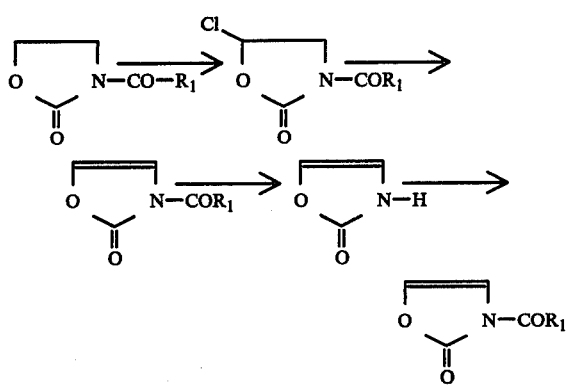

Examples which may be mentioned for R₁ are: as optionally substituted alkyl, C₁-C₈-alkyl, such as methyl, ethyl, propyl, n-butyl, iso-butyl, n-hexyl and n-octyl; C₁-C₄-alkyl which is substituted by C₁-C₂-alkoxy and C₁-C₄-alkyl which is substituted by halogen, such as chlorine or bromine; as optionally substituted alkenyl, in particular allyl, methallyl and cinnamyl; as optionally substituted cycloalkyl, above all C₅-C₆-cycloalkyl, such as cyclopentyl and cyclohexyl, and C₅-C₆-cycloalkyl which is substituted by C₁-C₄-alkyl groups, such as 4-methyl-cyclohexyl, 2,6-dimethyl-cyclohexyl and tert.-butyl-cyclohexyl; as optionally substituted aralkyl, above all benzyl and benzyl which is substituted by C₁-C₄-alkyl, C₁-C₂-alkoxy or halogen, especially chlorine, such as 4-methyl-, 4-methoxy-, 2-methyl-, 3-chloro-, 4-fluoro-, 4-chloro- and 4-tert.-butyl-benzyl; as optionally substituted aryl, above all phenyl and phenyl which is substituted by C₁-C₄-alkyl, C₁-C₂-alkoxy or halogen, especially chlorine, such as tolyl, xylyl, 4-methoxyphenyl, 2,4-dichlorophenyl, 4-chlorophenyl, 4-tert.-butylphenyl, 4-bromophenyl, 1- and 2-naphthyl and 4-benzoylphenyl; as alkoxy, above all C₁-C₄-alkoxy, such as methoxy, ethoxy, propoxy and butoxy; as aryloxy, above all phenoxy and phenoxy which is substituted by C₁-C₄-alkyl, C₁-C₂-alkoxy or halogen, especially chlorine; as alkylamino, above all C₁-C₈-alkylamino, such as methyl-, ethyl-, butyl- and 2-ethylhexyl-amino; as dialkylamino, above all di-C₁-C₈-alkylamino, such as dimethyl-, diethyl-, di-sec.-butyl-, di-amyl- and dioctylamino; and, as arylamino, above all phenylamino and phenylamino which is substituted by C₁-C₄-alkyl, C₁-C₂-alkoxy or halogen, espcially chlorine.

The 3-acyl-oxazolidin-2-ones, especially 3-acetyl-oxazolidin-2-one, which are required as starting compounds for the process according to the invention are in themselves known (see C.A. 40, 4,084 (1946)) or can be prepared according to known processes (Houben-Weyl, Methoden der org. Chemie XI/2, page 1 (1958) Georg Thieme-Verlag-Stuttgart; The chemistry of the amino group-Interscience Publ., J. Wily and Sons, page 278 (1968); Quart. Rev. (London) 17, 160 (1963)).

These 3-acyl-oxazolidin-2-ones ae chlorinated, optionally in the presence of a solvent which is inert under the reaction conditions, at a temperature from about 20° to about 150° C., preferably 50° and 100° C., in the presence of an agent which forms free radicals or of UV light and the chlorination product is then subjected to dehydrochlorination. The dehydrochlorination can be effected by heating in vacuo to about 100° to about 250° C. or by reaction with a tertiary amine in an aprotic solvent at temperatures between about 20° and about 100° C.

The starting compounds employed for the process according to the invention are those oxazolidin-2-ones acylated in the 3-position in which the acyl radical $R_1$ is essentially inert under the chlorinating conditions used. Examples which may be mentioned are: 3-propionyl-, 3-n-butyryl-, 3-methoxycarbonyl-, 3-ethoxycarbonyl-, 3-phenoxycarbonyl-, 3-dimethylaminocarbonyl- and 3-phenylaminocarbonyl-oxazolidin-2-one; 3-acetyl-oxazolidin-2-one is preferred.

Chlorine and sulphuryl chloride, as well as mixtures of chlorine and sulphuryl chloride, can be used for the chlorination. The chlorinating agent is usually employed in approximately equimolar amounts.

For the chlorination reaction, aprotic organic solvents, such as halogenated hydrocarbons, for example chloroform, methylene chloride or chlorobenzene, or carbon disulphide can be used as solvents which are inert under the reaction conditions; carbon tetrachloride has proved particularly suitable.

For the dehydrochlorination, aprotic organic solvents, such as ethers, for example diethyl ether, tetrahydrofurane, dioxane or 1,2-dimethoxyethane; esters, for example acetic acid esters of lower alcohols, such as ethyl acetate; or hydrocarbons, for example benzene and alkylbenzenes, can, in particular, be used as solvents which are inert under the reaction conditions.

Tertiary bases which have proved suitable for the dehydrohalogenation are trialkylamines such as triethylamine, N,N-dimethylcyclohexylamine, N,N-dimethylbenzylamine, N,N-dialkylanilines, such as N,N-dimethylaniline and N,N-diethylaniline, and heterocyclic bases, such as pyridine, picolines and diazabicycloalkenes, for example 1,5-diazabicyclo[4.3.0]-non-5-ene. Generally the tertiary bases are inserted in aequimolar and excess amounts. Preferably an excess of 25 to 35% is to be used. Triethylamine is preferably used as tertiary base.

The elimination of the acyl radical in the 3-position of the substituted $\Delta^4$-oxazolin-2-one can be carried out in the manner customary for the saponification of carboxylic acid amides using, for example, dilute aqueous alkaline solutions, for example 0.1 to 5 n NaOH or 0.1 to 5 n KOH, or 5 to 35% by weight ammonia, or by base-catalysed or acid-catalysed solvolysis in a lower alcohol ($C_1$ to $C_6$), for example methanol or ethanol, at temperatures of 20° to 100° C.

For elimination of the acetyl radical from 3-acetyl-$\Delta^4$-oxazolin-2-one, solvolysis in methanol, which is optionally catalysed by hydrogen chloride, at temperatures of 20° to 65° C. has proved particularly suitable.

Examples of basic solvolysis catalysts which may be mentioned are: alkali metal hydroxides, such as sodium hydroxide, and alkali metal alcoholates, such as sodium methylate or sodium ethylate, and examples of acid solvolysis catalysts which may be mentioned are: hydrogen chloride, sulphuric acid, p-toluenesulphonic acid and perchloric acid.

The reacylation of $\Delta^4$-oxazolin-2-one can be carried out in a manner which is in itself known by reacting the compound with acylating agents, such as acid anhydrides, acid chlorides, isocyanates or ketenes. By means of reacylation it is possible, in particular, to prepare those $\Delta^4$-oxazolin-2-ones of the formula I in which R represents an acyl radical which is sensitive to chlorination.

In general, the process according to the invention is carried out as follows: the oxazolidin-2-ones of the formula II, which are acylated in the 3-position, or their solutions in an aprotic solvent, preferably in carbon tetrachloride, are heated to the required reaction temperature and kept at this temperature during the subsequent addition of chlorine and/or sulphuryl chloride. The chlorination, which proceeds by a free radical mechanism, is started by adding an agent which forms free radicals, for example azoisobutyryldinitrile, or by UV light. Chlorine and/or sulphuryl chloride are metered in at the rate at which they are consumed and the rate of the addition can be controlled easily and simply with the aid of known methods of measurement, in accordance with the evolution of gas during the reaction. In general, the reaction mixture must be warmed in order to maintain the reaction temperature.

Working up of the reaction mixture, which in addition to the reaction product can also contain residues of the starting compound, hydrogen chloride and, in some cases, sulphur dioxide in solution, is carried out in a manner which is in itself known. For example, the products which have lower boiling points than the 3-acyl-5-chloro-oxazolidin-2-one can be distilled off, if appropriate under reduced pressure. However, it is also possible to wash out a large proportion of these products with water; the reaction product remains in the organic phase.

The crude reaction product which is obtained can optionally be purified by recrystallisation in an inert solvent, preferably n-hexan; however, it is usually employed direct for the dehydrohalogenation. Dehydrohalogenation by the action of heat is carried out, for example, by introducing the crude 3-acyl-5-chloro-oxazolidin-2-one dropwise into a flask which has been warmed to 100° to 250° C. and distilling off the resulting product under reduced pressure. The product is then purified in the customary way, for example by distillation, if appropriate under reduced pressure, or by recrystallisation.

Base-catalysed dehydrohalogenation is carried out, for example, by dissolving the crude 3-acyl-5-chloro-oxazolidin-2-one in an aprotic solvent, for example diethyl ether or 1,4-dioxane, and adding to the solution, at the boiling point of the solvent, about 1-3 mols of the tertiary base, per mol of chlorine compound, in portions, whilst stirring. In general, the elimination of hydrogen chloride is complete after 20-30 hours. After the hydrochloride has been separated off, 3-acyl-$\Delta^4$-oxazolin-2-one is isolated from the solution. The isolation and purification are carried out as indicated above, by distillation and/or recrystallisation.

Solvents which have proved suitable for recrystallisation of the 3-acyl-$\Delta^4$-oxazolin-2-ones are, in particular, mixtures of diethyl ether and alkanes, for example n-hexane. If necessary, the solution of the reaction product can be purified with the aid of customary clarifying agents or adsorbents, such as charcoal or kieselguhr, before crystallisation.

In order to prepare unsubstituted $\Delta^4$-oxazolin-2-one, the 3-acyl-$\Delta^4$-oxazolin-2-one, preferably the 3-acetyl derivative, is reacted with a lower alcohol in the presence of catalytic amounts of the corresponding sodium alcoholate, or in the presence of catalytic amounts of a mineral acid, preferably hydrogen chloride, at or below the boiling point of the alcohol used. The deacetylation can also be carried out by solvolysis in a lower alcohol without the addition of a mineral acid. However, experience has shown that longer reaction times are necessary for this.

$\Delta^4$-Oxazolin-2-one is isolated and purified by concentrating the reaction solution and recrystallising the residue, for example from ethyl acetate, ethyl acetate/petroleum ether, methanol or methanol/diethyl ether.

The $\Delta^4$-oxazolin-2-ones, according to the invention, of the general formula I are valuable starting compounds for numerous substitution and addition reactions. A particular feature of the compounds accessible with the aid of the $\Delta^4$-oxazolin-2-ones according to the invention is that they contain the structural elements of the 1,2-aminoalcohols which are interesting in many respects. The addition compounds which are obtained by a cycloaddition reaction under the action of heat (for example Diels-Alder reactions, 1,3-dipolar additions and carbene additions) are of particular interest, since hydrolysis of these addition compounds leads to 1,2-aminoalcohols of cyclic compounds in the cis configurations.

For example, 3-acetyl-$\Delta^4$-oxazolin-2-one reacts with numerous 1,3-dienes, for example butadiene, in some cases under mild reaction conditions, by a Diels-Alder reaction to give bicyclic or polycyclic N-acetyl-oxazolidin-2-ones. These compounds, in turn, can be deacetylated in a simple, gentle manner to give the corresponding oxazolidin-2-ones, or under more vigorous reaction conditions, can be hydrolysed to the particular 1,2-aminoalcohols. In these reactions, the cyclic 1,2-aminoalcohols are formed exclusively in the cis configurations.

These cis-1,2-aminoalcohols are, in turn, important starting compounds for the preparation of pharmaceuticals; for example, the reaction of cis-2-amino-cyclohexanol with p-toluenesulphonyl isocyanate leads to compounds which on oral administration display a hypoglycaemic action (see Swiss Patent Specification 487,918; Monatshefte 100, 2,122 et seq. (1969) and Helv. Chim. Acta 58, 1,781 (1975)).

A compound which has the same type of action is also obtained when 3-endo-amino-2-endo-bornanol is reacted with p-toluenesulphonyl isocyanate.

Hitherto, the cis-1,2-aminoalchols which are required for the preparation of the pharmaceuticals were accessible, if at all, only by involved processes. The $\Delta^4$-oxazolin-2-ones, according to the invention, of the formula I open up for the first time a simple route, which can be carried out even on an industrial scale, for the preparation of the cis-1,2-aminoalcohols which hitherto were accessible only with difficulty.

The $\Delta^4$-oxazolin-2-ones according to the invention can also be employed as vinyl monomers in homo- and co-polymerisations. In this way, polymers which contain oxazolidin-2-one rings and can find diverse use as antistatic agents, dyeing auxiliaries and ion exchangers are obtained. Poly-1,2-aminoalcohols are accessible therefrom by hydrolysis and can be used, for example, as emulsifiers and leather, dyeing and plastics auxiliaries; The compounds claimed according to the invention are distinguished from other copolymerisable N-vinyl compounds by the ease with which the cyclic urethane group is hydrolysed, with the formation of polyaminoalcohols, in corresponding polymers.

The following examples illustrate the invention without limitation to the embodiment referred to.

EXAMPLE 1

A solution of 129.0 g (1.0 mol) of 3-acetyloxazolidin-2-one in 850 ml of carbon tetrachloride is heated to 80° C. in a four-necked flask provided with a reflux condenser, an internal thermometer, a stirrer, a gas inlet tube and a dip tube. Dry chlorine gas is passed into this solution whilst internally irradiating with UV light (HPK 125 W mercury high-pressure burner). After 1.1 mols of $Cl_2$ have been taken up, the chlorination is discontinued. The solvent is distilled off under reduced pressure and 171 g of a pale yellow oil with a chlorine content of 18% (calculated: 21.7% of Cl) are obtained.

$^1$H—NMR (CDCl$_3$): $\tau$ = 3.6 (1H, CH), 5.5–5.2 (2H, CH$_2$) and 7.5 (3H, CH$_3$CO).

It follows from the analysis of the crude product ($^{13}$C—NMR (CDCl$_3$)), taken in conjunction with corresponding data for 3-acetyloxazolidin-2-one and for 1,3-diacetylimidazolidin-2-one, that the crude product from the chlorination consists to the extent of about 70% of 3-acetyl-5-chloro-oxazolidin-2-one.

EXAMPLE 2

1.2 g of azoisobutyrodinitrile and 74.5 g (0.55 mol) of sulphuryl chloride are introduced in the course of 2 hours into a boiling solution of 64.5 g (0.5 mol) of 3-acetyl-oxazolidin-2-one in 250 ml of chloroform, whilst stirring. After stirring at the reflux temperature for 3 hours, the solvent and excess sulphuryl chloride are distilled off under reduced pressure. 79 g of crude 3-acetyl-5-chloro-oxazolidin-2-one remain as the residue in the form of a light brown clear oil with a chlorine content of 15.4% (calculated: 21.7% of Cl).

This crude chlorination product (79.0 g) is introduced dropwise into a flask which has been heated to 160°–180° C. and the reaction products which form are continously distilled off under a reduced pressure of 24 mm Hg. Fractional distillation of the pyrolysis product gives 29 g (45% of theory) of 3-acetyl-$\Delta^4$-oxazolin-2-one (boiling point: 114°–116° C./22mm Hg).

EXAMPLE 3

135 g (1.33 mol) of triethylamine are added dropwise to a boiling solution of the crude 3-acetyl-5-chloro-oxazolidin-2-one (171.0 g) obtained according to Example 1 in 200 ml of dry diethyl ether, whilst stirring. After stirring at the reflux temperature for 48 hours, the reaction mixture is filtered, the triethylamine hydrochloride which has been separated off is washed with ether and the combined filtrates are concentrated. Fractional distillation under reduced pressure gives 77 g (60% of theory) of a colourless oil (boiling poing: 110° C./14 mm Hg) which solidifies in the receiver. After crystallisation from diethyl ether, 3-acetyl-$\Delta^4$-oxazolin-2-one is obtained in the form of colourless crystals with a melting point of 35°–37° C.

Empirical formula C$_5$H$_5$NO$_3$; Molecular weight 127.1

| | | | | |
|---|---|---|---|---|
| Calculated. | C 47.25 | H 3.97 | N 11.02 | O 37.76 |
| Found. | 46.75 | 3.83 | 11.05 | 37.7 |

UV (CH$_2$Cl$_2$): $\lambda_{max}$ (log $\epsilon$) 238 nm (3.84)
IR (CCl$_4$): 1,800 and 1,735 cm$^{-1}$ (CO)
$^1$H—NMR (CDCl$_3$): $\tau$ = 2.72 (doublet, 1H), 3.07 (doublet, 1H, J = 2.4 Hz) and 7.42 (singlet, 3H, CH$_3$).

Hydrogenation of 1.27 g (0.01 mol) of 3-acetyl-Δ⁴-oxazolin-2-one in 25 ml of ethyl acetate at 20° C., using palladium-on-charcoal as the catalyst, gives, after the customary working up, 1.28 g of colourless crystals (melting point: 70°–72° C.) which show no depression of the melting point when mixed with an authentic sample of 3-acetyloxazolidin-2-one.

EXAMPLE 4

A crude chlorination product (123.0 g), obtained in a manner analogous to Example 1 from 96.8 g (0.75 mol) of 3-acetyl-oxazolidin-2-one, is heated to 120°–150° C., under nitrogen. After the evolution of hydrogen chloride has subsided (4 hours), the product is subjected to fractional distillation under reduced pressure and 69.3 g (73% of theroy) of 3-acetyl-Δ⁴-oxazolin-2-one (boiling point: 116° C/24 mm Hg) are obtained. The product is identical with the preparation produced according to Example 3.

EXAMPLE 5

A solution of 12.7 g (0.1 mol) of pure, recrystallised 3-acetyl-Δ⁴-oxazolin-2-one in 50 ml of anhydrous methanol is heated to the reflux temperature for 26 hours. The course of the saponification reaction is followed by thin layer chromatography. After the saponification has ended, the solution is concentrated to dryness by distillation in vacuo (15 mm Hg). 8.5 g of Δ⁴-oxazolin-2-one (melting range: 102°–107° L C.) are obtained. After the crude product has been recrystallised from ethyl or methanol/diethyl ether, Δ⁴-oxazolin-2-one is obtained in the form of colourless needles (melting point 111°–113° C.).

Empirical formula $C_3H_3NO_2$; Molecular weight 85.1

| | | | | |
|---|---|---|---|---|
| Calculated. | C 42.36 | H 3.55 | N 16.47 | O 37.62 |
| Found. | 42.8 | 3.44 | 16.3 | 36.6 |

¹H—NMR (CDCl₃): τ = 0.25 (multiplet, 1H, NH), 3.15 (doublet, 1H) and 3.32 (doublet, 1H, J ~ 1.5 Hz).
IR (KBr): 3,200 (NH), 1,740 and 1,765 (CO) cm⁻¹.

Hydrogenation of 1.7 g (0.02 mol) of Δ⁴-oxazolin-2-one in 25 ml of ethyl acetate at 20° C. using palladium-on-charcoal as the catalyst gives oxazolidin-2-one (melting point: 86°–88° C.), which is known.

EXAMPLE 6

A solution of 63.5 g (0.5 mol) of crude 3-acetyl-Δ⁴-oxazolin-2-one (chlorine-containing; chlorine content: 0.68% by weight) in 300 ml of methanol is heated to the reflux temperature until conversion is complete (about 6 hours). The solvent is distilled off under reduced pressure and the crystalline residue is recrystallised from methanol/diethyl ether. 40.5 g of Δ⁴-oxazolin-2-one are obtained in the form of colourless needles (melting point: 103°–106° C.).

The solvolysis proceeds in the same way when it is carried out with pure cyrstallised 3-acetyl-Δ⁴-oxazolin-2 -one in 0.003 N methanolic hydrochloric acid.

EXAMPLE 7

A solution of 4.4 g (0.052 mol) of Δ⁴-oxazolin-2-one in 80 ml of acetic anhydride is heated to the reflux temperature for 4 hours. After the excess acetic anhydride has been distilled off under reduced pressure, 4 g (61% of theory) of 3-acetyl-Δ⁴-oxazolin-2-one are obtained in the form of colourless crystals (melting point: 35°–38° C.; from diethyl ether). It follows from the fact that the ¹H—NMR and IR spectra of this compound and of the 3-acetyl-Δ⁴-oxazolin-2-one obtained according to Example 3 are the same that the two compounds are identical.

EXAMPLE 8

5 ml of pyridine are added to a mixture of 2.55 g (0.03 mol) of Δ⁴-oxazolin-2-one and 5.6 g (0.04 mol) of benzoyl chloride in 50 ml of chloroform, whilst cooling. After standing overnight at 20° C., the batch is poured onto ice and the crystals which have precipitated are separated off. Yield: 4.3 g (75%) of 3-benzoyl-Δ⁴-oxazolin-2-one. Melting point: 93°–95° C. (from ether).

| $C_{10}H_7NO_3$ (189.2) | | | |
|---|---|---|---|
| Calculated. | C 63.49 | H 3.73 | N 7.41 |
| Found. | 63.5 | 3.61 | 7.42 |

IR (KBr): 1,800 and 1,680/cm (CO)
¹H—NMR (DCDl₃): τ = [2.4 (m, C₆H₅), 2.8 (d, CH) 6H]; 2.2 ppm (d, CH, 1H).

The following 3-acyl-Δ⁴-oxazolin-2-ones were obtained in the same way: 3-(p-chlorobenzoyl)-Δ⁴-oxazolin-2-one, 3-p-toluyl-Δ⁴-oxazolin-2-one, 3-propionyl-Δ⁴-oxazolin-2-one, 3-n-butyryl-Δ⁴-oxazolin-2-one, 3-(p-methoxybenzoyl)-Δ⁴-oxazolin-2-one, 3-(α-naphthoyl)-Δ⁴-oxazolin-2-one, 3-(p-phenylbenzoyl)-Δ⁴-oxazolin-2-one, 3-chloroacetyl-Δ⁴-oxazolin-2-one, 3-phenyl-acetyl-Δ⁴-oxazolin-2-one, 3-iso-butyryl-Δ⁴-oxazolin-2-one, 3-acryloyl-Δ⁴-oxazolin-2-one, 3-methacryloyl-Δ⁴-oxazolin-2-one and 3-dichloroacetyl-Δ⁴-oxazolin-2-one.

EXAMPLE 9

5 ml of pyridine are added to a solution of 2.55 g (0.03 mol) of Δ⁴-oxazolin-2-one and 6.3 g (0.04 mol) of chloroformic acid phenyl ester in 50 ml of chloroform, whilst cooling with ice. After standing overnight at 20° C., and after water has been added, the precipitate which has deposited is separated off and recrystallised from chloroform/ether (6.1 g, corresponding to 99%, of 3-phenoxycarbonyl-Δ⁴-oxazolin-2-one). Melting point: 106°–107° C.

| $C_{10}H_7NO_4$ (205.2) | | | |
|---|---|---|---|
| Calculated. | C 58.54 | H 3.44 | N 6.83 |
| Found. | 58.9 | 3.27 | 6.81 |

IR (KBr): 1,820 and 1,740/cm (CO)
¹H—NMR (CDCl₃): τ = [2.67 (m, C₆H₅), 2.85 (d, CH) 6 H]; 7.15 ppm (d, CH, 1H)

The following 3-acyl-Δ⁴-oxazolin-2-ones were obtained in the same way: 3-methoxy-carbonyl-Δ⁴-oxazolin-2-one, 3-ethoxy-carbonyl-Δ⁴-oxazolin-2-one, 3-dimethylaminocarbonyl-Δ⁴-oxazolin-2-one, 3-(p-tolyloxycarbonyl)-Δ⁴-oxazolin-2-one and 3-n-butoxycarbonyl-Δ⁴-oxaxolin-2-one.

EXAMPLE 10

After adding 0.1 g of hydroquinone, a solution of 127 g (1.0 mol) of 3-acetyl-Δ⁴-oxazolin-2-one and 54 g (1.0 mol) of buta-1,3-diene in 200 ml of benzene is heated to 160°–170° C. in a Carius tube for 24 hours. After distilling off the solvent and distilling the residue, 109 g (60% of theory) of cis-4-acetyl-2-oxa-4-aza-bicyclo[4.3.0]non-7-en-3-one are obtained in the form of a colourless liquid (boiling point: 105° C./0.45 mm Hg; $n_D^{20}$: 1.5088, melting point: 33°–34° C. (from ether)).

Empirical formula $C_9H_{11}NO_3$; Molecular weight 181.2

| Calculated. | C 59.66 | H 6.12 | N 7.73 |
|---|---|---|---|
| Found. | 59.71 | 6.30 | 7.92 |

IR (film): 1,780 and 1,700/cm (CO)
$^1$H—NMR (CDCl$_3$): $\tau$ = 7.6 (multiplet, 4H), 7.51 (singlet, 3H, CH$_3$), 5.2 (multiplet, 2H) and 4.05 (multiplet, 2 olefinic H).

EXAMPLE 11

181 g (1.0 mol) of cis-4-acetyl-2-oxa-4-aza-bicyclo[4.3.0]non-7-en-3-one, in 1,000 ml of methanol, are hydrogenated at 25° C. under normal pressure in the presence of platinum dioxide. After the catalyst has been filtered off, the reaction solution is freed from the solvent by distillation. Distillation of the residue gives 183 g (100% of theory) of cis-4-acetyl-2-oxa-4-aza-bicyclo[4.3.0]nonan-3-one (melting point: 80°–83° C.; from methanol).

Empirical formula $C_9H_{13}NO_3$; Molecular weight 183.2

| Calculated. | C 59.00 | H 7.15 | N 7.65 |
|---|---|---|---|
| Found. | 58.90 | 7.38 | 7.83 |

IR (film): 1,760 and 1,680/cm (CO)
$^1$H—NMR (CDCl$_3$): $\tau$ = 8.4 (multiplet, 8H), 7.52 (singlet, 3H, CH$_3$) and 5.6 (multiplet, 2H).

EXAMPLE 12

After adding 5 g of sodium methylate, a solution of 183 g (1 mol) of cis-4-acetyl-2-oxa-4-aza-bicyclo[4.3.0]nonan-3-one in anhydrous methanol is heated to the reflux temperature for 5 hours. After the solvent has been distilled off, the residue is recrystallised from diethyl ether. 116 g (82% of theory) of cis-2-oxa-4-aza-bicyclo[4.3.0]nonan-3-one (melting point: 56°–58° C.) are obtained. (See J. Org. Chem. 32, 540 (1967); melting point: 55°–56° C.).

Empirical formula $C_7H_{11}NO_2$; Molecular weight 141.2

| Calculated. | C 59.55 | H 7.85 | N 9.92 |
|---|---|---|---|
| Found. | 59.81 | 7.97 | 9.67 |

IR (KBr): 1,728 and 1,708/cm (CO)
$^1$H—NMR (CDCl$_3$): $\tau$ = 8.3 (multiplet, 8H), 6.25/5.4 (multiplet, 2H) and 3.3 (singlet, 1H, NH).

EXAMPLE 3

A solution of 181 g (1 mol) of cis-4-acetyl-2-oxa-4-aza-bicyclo[4.3.0]non-7-en-3-one and 336 g (6 mols) of potassium hydroxide in 1,200 ml of methanol and 600 ml of water is heated to the reflux temperature for 30 hours and is then exhaustively extracted with diethyl ether. Separation of the ether extract into neutral and basic compounds, which is carried out in the customary manner, gives 85 g (75% of theory) of cis-2-aminocyclohex-4-en-1-ol (melting point: 58°–60° C.; from ether/pentane).

Empirical formula $C_6H_{11}NO$; Molecular weight 113.2

| Calculated. | C 63.68 | H 9.80 | N 12.39 |
|---|---|---|---|
| Found. | 63.3 | 9.36 | 12.4 |

$^1$H—NMR (CDCl$_3$): $\tau$ = 7.8 (multiplet, 4H), 7.45 (broad singlet, 3H, OH and NH$_2$), 7.0/6.2 (multiplet 2H) and 4.4 (multiplet, 2 olefinic H) N-benzoyl derivative: melting point: 150° C., from ethanol/diethyl ether).

EXAMPLE 14

113 g (1 mol) of cis-2-aminocyclohex-4-en-1-ol in 500 ml of methanol are hydrogenated under normal pressure at 25° C. in the presence of palladium (5% Pd/C). After filtering off the catalyst and distilling off the solvent, 110 g of cis-2-aminocyclohexan-1-ol (melting point: 72°–76° C.; from methanol) are obtained. (J. Amer. Chem. Soc. 71, 637 (1949): melting point: 72°–73° C.).

N-Benzoyl derivative: melting point: 183°–184° C. (from ethanol).

EXAMPLE 15

A solution of 4.25 g (0.05 mol) of $\Delta^4$-oxazolin-2-one and 5.95 g (0.05 mol) of phenyl isocyanate in 20 ml of dimethylformamide is kept at 50° C. for 8 hours. After adding water, the precipitate which has deposited is separated off and recrystallised from diethyl ether.

(9.0 g correspond to 88% of 3-phenylcarbamoyl-$\Delta^4$-oxazolin-2-one)

Melting point 110° to 112° C., colourless crystals. $C_{10}H_8N_2O_3$ (204.14)

| Calculated. | C 58.83 | H 3.95 | N 13.73 |
|---|---|---|---|
| Found. | 58.6 | 4.0 | 13.7 |

IR (KBr): 1,755 and 1,725/cm (CO)
$^1$H—NMR (CDCl$_3$): $\tau$ = 0.8 (m, NH, 1H); [2.6 (m, C$_6$H$_5$); 2.8 (d, CHO) 6H] and 3.08 ppm (d, CHN, 1H).

What is claimed is:
1. A $\Delta^4$-oxazolin-2-one of the formula

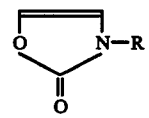

I in which
R is an acyl radical of the formula R$_1$—CO—,
in which
R$_1$ is C$_1$–C$_8$-alkyl; C$_1$–C$_4$-alkyl substituted by C$_1$–C$_2$-alkoxy or halogen; allyl, methallyl or cinnamyl; C$_5$–C$_6$-cycloalkyl; C$_5$–C$_6$-cycloalkyl substituted by C$_1$–C$_4$ alkyl; benzyl; benzyl substituted by C$_1$–C$_4$-alkyl, C$_1$–C$_2$-alkoxy or halogen; phenyl; phenyl substituted by C$_1$–C$_4$-alkyl, C$_1$–C$_2$-alkoxy or halogen; 1- or 2-naphthyl, 4-benzoylphenyl; C$_1$–C$_4$-alkoxy; phenoxy; phenoxy substituted by C$_1$–C$_4$-alkyl, C$_1$–C$_2$-alkoxy or halogen; C$_1$–C$_8$-alkylamino; di-C$_1$–C$_8$-alkylamino; phenylamino; or phenylamino substituted by C$_1$–C$_4$-alkyl, C$_1$–C$_2$-alkoxy or halogen.

2. A compound of claim 1 said compound being 3-acetyl-$\Delta^4$-oxazolin-2-one.

* * * * *

UNITED STATES PATENT AND TRADEMARK OFFICE
CERTIFICATE OF CORRECTION

PATENT NO. : 4,130,563
DATED : December 19, 1978
INVENTOR(S) : Karl-Heinz Scholz, et al.

It is certified that error appears in the above-identified patent and that said Letters Patent are hereby corrected as shown below:

Patent, column 2, line 64, "ae" should be --are--.

Column 5, line 46, "aminoalchols" should be --aminoalcohols--.

Column 6, line 38, "continously" should be --continuously--.

Column 6, line 40, delete "66" and insert -- Δ --. after "acetyl-".

Column 6, line 55, delete "66" and insert -- Δ --. after "acetyl-".

Column 7, line 16, "theroy" should be --theory--.

Column 7, line 30, insert --acetate-- after "ethyl".

UNITED STATES PATENT AND TRADEMARK OFFICE
CERTIFICATE OF CORRECTION

PATENT NO. : 4,130,563
DATED : December 19, 1978
INVENTOR(S) : Karl-Heinz Scholz, et al.

It is certified that error appears in the above-identified patent and that said Letters Patent are hereby corrected as shown below:

Column 7, line 56, "coluorless" should be --colourless--.
Column 7, line 59, "cyrstallised" should be --crystallised--.
Column 9, line 58, "3" should be --13--.

Signed and Sealed this

Tenth Day of July 1979

[SEAL]

Attest:

*Attesting Officer*

LUTRELLE F. PARKER
*Acting Commissioner of Patents and Trademarks*